(12) United States Patent
Neuwirth (10) Patent No.: US 6,187,346 B1
(45) Date of Patent: *Feb. 13, 2001

(54) INTRAUTERINE CHEMICAL CAUTERIZING METHOD AND COMPOSITION

(75) Inventor: Robert S. Neuwirth, Englewood, NJ (US)

(73) Assignee: Ablation Products, Inc., Englewood, NJ (US)

( * ) Notice: Under 35 U.S.C. 154(b), the term of this patent shall be extended for 0 days.

This patent is subject to a terminal disclaimer.

(21) Appl. No.: 08/895,424

(22) Filed: Jul. 15, 1997

Related U.S. Application Data (63) Continuation of application No. 08/486,561, filed on Jun. 7, 1995, now abandoned.

(51) Int. Cl.$^7$ ............................ A61K 33/38; A61K 31/28
(52) U.S. Cl. ......................... 424/618; 424/619; 514/495
(58) Field of Search .................... 424/618, 619; 514/495

(56) References Cited

U.S. PATENT DOCUMENTS

| | | | |
|---|---|---|---|
| 1,652,954 | 12/1927 | Pierce | 607/105 |
| 2,190,384 | 2/1940 | Newman | 607/105 |
| 2,355,231 | 8/1944 | Moore | 604/20 |
| 3,174,481 | 3/1965 | Seaman | 128/401 |
| 3,394,705 | 7/1968 | Abramson | 128/349 |
| 3,459,175 | 8/1969 | Miller | 128/2 |
| 3,540,451 | 11/1970 | Zemma | 128/334 |
| 3,803,308 | 4/1974 | Zipper et al. | 424/140 |
| 3,817,248 | 6/1974 | Buckles et al. | 128/260 |
| 3,822,702 | 7/1974 | Bolduc | 128/235 |
| 3,848,602 | 11/1974 | Gutnick | 128/341 |
| 3,875,939 | 4/1975 | Bolduc et al. | 128/235 |
| 3,887,112 | 6/1975 | Bolduc et al. | 222/85 |
| 3,924,628 | 12/1975 | Droegemueller et al. | 128/303.1 |
| 3,948,259 | 4/1976 | Bolduc et al. | 128/235 |
| 3,964,477 | 6/1976 | Ellis et al. | 128/172.1 |
| 3,972,331 | 8/1976 | Bolduc et al. | 128/232 |
| 4,012,839 | 3/1977 | Hill | 32/15 |
| 4,071,027 | 1/1978 | Meador | 128/231 |
| 4,109,654 | 8/1978 | Bolduc et al. | 128/235 |
| 4,119,098 | 10/1978 | Bolduc et al. | 128/235 |
| 4,126,134 | 11/1978 | Bolduc et al. | 128/235 |
| 4,137,922 | 2/1979 | Leininger et al. | 128/344 |
| 4,160,446 | 7/1979 | Barrington | 128/1 R |
| 4,185,618 * | 1/1980 | Corey | 128/1 R |
| 4,293,536 | 10/1981 | Jensen et al. | 424/1 |
| 4,430,607 | 2/1984 | Harris | 604/96 |
| 4,585,438 | 4/1986 | Makler | 604/106 |
| 4,601,698 | 7/1986 | Moulding, Jr. | 604/55 |
| 4,637,818 | 1/1987 | Johnson et al. | 604/89 |
| 4,773,899 | 9/1988 | Spears | 604/20 |
| 4,857,555 | 8/1989 | Smith et al. | 514/563 |
| 4,863,932 | 9/1989 | Sinensky et al. | 514/307 |
| 4,891,043 | 1/1990 | Zeimer et al. | 604/20 |
| 5,030,202 | 7/1991 | Harris | 604/27 |
| 5,039,704 | 8/1991 | Smith et al. | 514/563 |
| 5,063,065 | 11/1991 | Bazterrica et al. | 424/637 |
| 5,066,659 * | 11/1991 | Lipinski | 514/278 |
| 5,100,388 | 3/1992 | Behl et al. | 604/113 |
| 5,104,377 | 4/1992 | Levine | 604/101 |
| 5,105,808 | 4/1992 | Neuwirth et al. | 128/401 |
| 5,163,905 | 11/1992 | Don Michael | 604/101 |
| 5,170,774 | 12/1992 | Heckele | 128/4 |
| 5,174,304 | 12/1992 | Latina et al. | 128/793 |
| 5,188,602 | 2/1993 | Nichols | 604/113 |
| 5,192,688 | 3/1993 | Switzer, III et al. | 436/36 |
| 5,195,965 | 3/1993 | Shantha | 604/54 |
| 5,242,390 | 9/1993 | Goldrath | 604/55 |
| 5,242,437 | 9/1993 | Everett et al. | 606/15 |
| 5,256,139 | 10/1993 | Ghodsian | 604/19 |
| 5,257,977 | 11/1993 | Eshel | 604/113 |
| 5,279,542 | 1/1994 | Wilk | 604/19 |
| 5,282,785 | 2/1994 | Shapland et al. | 604/21 |
| 5,286,254 | 2/1994 | Shapland et al. | 604/21 |
| 5,290,763 | 3/1994 | Poser et al. | 514/21 |
| 5,298,018 | 3/1994 | Narcisco, Jr. | 604/21 |
| 5,300,023 | 4/1994 | Lowery et al. | 604/51 |
| 5,304,214 | 4/1994 | DeFord et al. | 607/105 |
| 5,306,249 | 4/1994 | Don Michel | 604/101 |
| 5,364,375 | 11/1994 | Swor | 604/278 |
| 5,371,191 | 12/1994 | Poser et al. | 530/350 |
| 5,372,584 | 12/1994 | Zink et al. | 604/55 |
| 5,380,317 | 1/1995 | Everett et al. | 606/15 |
| 5,397,803 | 3/1995 | Smith et al. | 514/563 |
| 5,403,309 | 4/1995 | Coleman et al. | 606/20 |
| 5,403,311 | 4/1995 | Abele et al. | 606/49 |
| 5,423,807 | 6/1995 | Milder | 606/20 |
| 5,431,662 | 7/1995 | Nicholas | 606/119 |
| 5,433,708 | 7/1995 | Nichols et al. | 604/13 |

(List continued on next page.)

FOREIGN PATENT DOCUMENTS

92/19145   11/1992   (WO) .

OTHER PUBLICATIONS

Nechay et al., "Inhibition of Adenosine Triphosphates In Vitro By Silver Nitrate Silver Sulfadiazine", Journal of Environmental Pathology, Toxicology, and Oncology, vol. 5, No. 4–5, pp. 119–126 (1984) (Abstract).

(List continued on next page.)

*Primary Examiner*—Theodore J. Criares
(74) *Attorney, Agent, or Firm*—Kenyon & Kenyon (57) ABSTRACT

A method and composition for effecting necrosis of a tissue lining of a mammalian body cavity, particularly a uterine endometrium, by introducing an applicator comprising a hysteroscope housing a first and a second catheter connected to a catheter into the uterus, distending the uterus by introducing $CO_2$ gas under pressure, delivering a silver nitrate paste to the endometrium through the first catheter and allowing the paste to remain a sufficient amount of time to substantially cauterize the entirety of the tissue lining, particularly the endometrium and delivering an aqueous sodium chloride solution to the uterus through the second catheter thereby neutralizing the silver nitrate and rinsing the uterine cavity.

15 Claims, 6 Drawing Sheets

U.S. PATENT DOCUMENTS

| | | | |
|---|---|---|---|
| 5,434,247 | 7/1995 | Jones | 530/328 |
| 5,435,805 | 7/1995 | Edwards et al. | 604/22 |
| 5,437,660 | 8/1995 | Johnson et al. | 606/15 |
| 5,445,961 | 8/1995 | Genovesi et al. | 435/240.5 |
| 5,451,208 | 9/1995 | Goldrath | 605/55 |
| 5,453,086 | 9/1995 | Weber | 604/20 |
| 5,891,457 | * 4/1999 | Neuwirth | 424/430 |

OTHER PUBLICATIONS

Nechay et al., "Inhibition of Adenosine Triphosphates In Vitro By Silver Nitrate And Silver Sulfadiazine", Journal of the American College of Toxicology, vol. 3, No. 1, pp. 37–42 (1984) (Abstract).

Williams et al., "Chemical Injury of Arteries", Journal of Pathology and Bacteriology, vol. 77, pp. 63–69 (1959) (Abstract).

No author, Silver nitrate wart treatment available OTC; Launches Avoca, a silver nitrate pencil for wart removal, Chemist & Druggist, 94–07–16, pp. 38 (1994) (Abstract).

No author, "Novel Biocide Design Using an Inorganic Composite", Speciality Chemicals, 94–06, pp. 223 (1994) (Abstract).

No author, "Spectrum Chemical and Safety Products", pp. S–xii, C–392–C–393 (1993–1994).

Richart et al., "Single–application fertility–regulating device: Description of a new instrument", Obstet. Gynecol. 127:86, 1977.

Paul et al., "Transvaginal Human Sterilization: A Preliminary Report", ASC Symposium Series 33, American Chemical Society, Washington, D.C., 1976.

Gregor et al., "Fallopian Tube Cauterization by Silver Ion–Polymer Gels", Controlled Release Polymeric Formulations, pp. 147–156.

Thompson et al., "Evaluation of Experimental Methods of Occluding the Uterotubal Junction", Female Sterilization (Prognosis for Simplified Outpatient Procedures), Academic Press, 1972, pp. 107–123.

Martens, F., "Attempted Cyrosurgical Closure of the Fallopian Tubes", Human Sterilization (A Conference), Charter 26, pp. 305–312, Charles C. Thomas, Springfield, Ill.

Stevenson et al., "The Effect of Methyl Cyanoacrylate Tissue Adhesive on the Human Fallopian Tube and Endometrium," The Journal of Obstetrics and Gynaecology of the British Commonwealth, Nov. 1972, vol. 79, pp. 1028–1039.

Mullick et al., "Studies of Quinacrine and of Tetracycline for Non–surgical Female Sterilization", Indian Rural Medical Association, Adv Contracept (England), Sep. 1987, pp. 245–254 (Abstract).

Bhatt et al., "Four Year Follow Up of Insertion of Quinacrine Hydrochloride Pellets as a Means of Nonsurgical Female Sterilization", Fertil Steril (United States), Sep. 1985, pp. 303–306 (Abstract).

Chandra, "Toxic Effects of Quinacrine Hydrochloride in Rhesus Monkeys", Contraception (United States), Sep. 1981, pp. 269–274 (Abstract).

Dubin et al., "Effect of Intrauterine Administration of Tetracyclines of Cynomolgus Monkeys", Contraception (United States), Jun. 1984, pp. 561–571 (Abstract).

Dubin et al., "Comparative Effects of Intrauterine Instillation of Analogues of Quinacrine and Tetracycline on Uterine Morphology in the Rat", Contraception (United States), Jun. 1984, pp. 553–559 (Abstract).

Dubin et al., "Pharmacokinetic Studies on Quinacrine Following Intrauterine Administration to Cynomolgus Monkeys", Fertil Steril (United States), Dec. 1982, pp. 735–740 (Abstract).

Laufe, et al., "Nonsurgical Female Sterilization", Intl J Gynaecol Obstet (United States), 1980, pp. 334–339 (Abstract).

Merchant et al., "Clinicopathologic Study of Fallopian Tube Closure After Single Transcervial Insertion of Quinacrine Pellets", Obstetrics and Gynecology, B.Y.L. Nair Hospital, Bombay, India, Int J Fertil Menopausal Stud (United States), Jan.–Feb. 1995, pp. 47–54 (Abstract).

Mukherjee et al., "Fluorescence of X and Y Chromatin in Human Interphase Cells", Cytogenetics (Switzerland), 1972, pp. 216–227 (Abstract).

Patek, "Quinacrine Hydrochloride. Review and Mode of Action of an Antimalarial, Used as an Occlusive Agent for Transvaginal Human Sterilization", Acta Obstet Gynecol Scand (Sweden), 1979, pp. 561–564 (Abstract).

Pollack et al., "Association for Voluntary Surgical Contraception: A Technical Statement on Quinacrine Pellets for Nonsurgical Female Sterilization", Association for Voluntary Surgical Contraception, New York, NY 10016, Adv Contracept (Netherlands), Mar. 1994, pp. 43–50 (Abstract).

Schenker et al., "Regeneration of Rabbit Endometrium Following Intrauterine Installation of Chemical Agents", Gynecol Invest (Switzerland), 1973, pp. 1–13 (Abstract).

Zaneveld et al., "Lack of Tubal Occlustion by Intrauterine Quinacrine and Tetracycline in the Primate", Contraception (United States), Aug. 1984, pp. 161–167 (Abstract).

Zimmerman et al., "Antifertility Effects of Tetradecyl Sodium Sulphate in Rabbits", J Reprod Fertil (England), Jul. 1983, pp. 257–263 (Abstract).

Zook et al., "Malignant Neoplasms of Decidual Origin (Decidusarcomas) Induced by Estrogen–Progestin–Releasing Intravaginal Device in Rabbits", Am J Pathol (United States), Aug. 1987, pp. 315–327 (Abstract).

Dubin et al., "Intrauterine Ethanol–Induced Termination of Pregnancy in Cynomolgus Monkeys (*Macaca fascicularis*)", Am J Obstet Gynecol (United States), Dec. 1, 1978, pp. 783–790 (Abstract).

Frazer et al., "Histopathologic Effects of Dimethyl Sulfoxide on Equine Endometrium", Department of Veterinary Clinical Sciences, College of Veterinary Medicine, Ohio State University, Columbus 43210, Am J Vet Res (United States), Oct. 1988, pp. 1774–1781 (Abstract).

Boto et al., "Surgical Alternatives to Hysterectomy for Intractable Menorrhagia", British Journal of Hospital Medicine, vol. 44, Aug. 1990, pp. 94–99.

Corfman, "Transcervical Oviduct Occlusion", Acting Director, Reproduction Program, National Institute of Child Health and Human Development, United States Public Health Service, Washington, D.C., pp. 183–187.

Corfman et al., "Response of the Rabbit Oviduct to a Tissue Adhesive", Science, vol. 14, Jun. 1965, pp. 1348–1350.

Corfman et al., "An Instrument for Transcervical Treatment of the Oviducts and Uterine Cornua", Obstetrics & Gynecology, vol. 27, No. 6, Jun. 1996.

DeCherney et al., "Endometrial Ablation for Intractable Uterine Bleeding: Hysteroscopic Resection", Obstetrics & Gynecology, vol. 70, No. 4, Oct. 1987, pp. 668–670.

Davis et al., "Fallopian Tube Occlusion in Rabbits with Silicone Rubber", The Journal of Reproductive Medicine, vol. 14, No. 2, Feb. 1975, pp. 56–61.

Droegemueller et al., "Cryocoagulation of the Endometrium at the Uterine Cornua", American Journal of Obstetrics and Gynecology, vol. 131, No. 1, May 1, 1978, pp. 1–9.

Dubin et al., "Effect of Intrauterine and Intravascular Quinacrine Administration on Histopathology, Blood Chemistry, and Hematology in Cynomolgus Monkeys", Fertility and Sterility, vol. 38, No. 6, Dec. 1982, pp. 741–747.

Goldrath et al., "Intrauterine Laser Surgery", Chapter 8, pp. 93–110.

Hill et al., "Intrauterine Surgery Using Electrocautery", Aust NZ J Obstet Gynaecol, 1990, pp. 145–146.

Imlach, "Edmonton Gynecologist at Legal Odds with Provincial College", CMA Journal, Jun. 7, 1975, vol. 112, pp. 1348 and 1355.

Laufe et al., "Nonsurgical Female Sterilization", Int J Gynaecol Obstet, vol. 18, 1980, pp. 333–339.

Magos, "Management of Menorrhagia", BMJ, vol. 300, Jun. 16, 1990, pp. 1537–1538.

Martin et al., "An Alternative to Hysterectomy Endometrial Laser Ablation", The British Journal of Theatre Nursing, May 1990, pp. 10–11.

Neuwirth et al., "Chemical Induction of Tubal Blockade in the Monkey", Obstetrics & Gynecology, vol. 328, No. 1, Jul. 1971, pp. 51–54.

Omran et al., "Tubal Occlusion: A Comparative Study", International Journal of Fertility, Oct.–Dec. 1970, vol. 15, No. 4, pp. 226–244.

Phipps et al., "Treatment of Functional Menorrhagia by Radiofrequency–Induced Thermal Endometrial Ablation", The Lancet, Feb. 17, 1990, 374–376.

Pitkin, "Sodium Morrhuate for Tubal Sterilization", Obstetrics & Gynecology, vol. 28, No. 5, Nov. 1966, pp. 680–683.

Richart, "Female Sterilization Using Chemical Agents", Research Frontiers in Fertility Regulation, Dec. 1981, vol. 1, No. 5, pp. 1–12.

Richart et al., "Female Sterilization by Electrocoagulation of Tubal Ostia Using Hysteroscopy", Am. J. Obstet. Gynecol., Nov. 15, 1973, pp. 801–804.

Ringrose, "Office Tubal Sterilization", Obstetrics & Gynecology, vol. 42, No. 1, Jul. 1973, pp. 151–155.

Richart, "The Use of Chemical Agents in Female Sterilization", Female Transcervical Sterilization, pp. 24–34.

Zipper et al., "Alterations in Fertility Induced by Unilateral Intrauterine Instillation of Cytotoxic Compounds in Rats", Am. J. Obst. & Gynce., Aug. 1, 1968, pp. 971–978.

Zipper et al., "Intrauterine Instillation of Chemical Cytotoxic Agents for Tubal Sterilization and Treatment of Functional Metrorrhagias", International Journal of Fertility, Oct.–Dec. 1969, vol. 14, No. 4, pp. 280–288.

Zipper et al., "Human Fertility Control by Transvaginal Application of Quinacrine on the Fallopian Tube", Fertility and Sterility, vol. 21, No. 8, Aug. 1970, pp. 581–589.

Laufe et al., "Nonsurgical Female Sterilization", Int J Gynaecol Obstet (United States), 1980, pp. 334–339 (Abstract).

Richart et al., "Intrauterine Administration of Methyl Cyanoacrylate as an Outpatient Method of Permanent Female Sterilization", Am J Obstet Gynecol (United States), Apr. 1987, pp. 981–987.

No author, The Use of Methyl Cyanoacrylate (MCA) for Female Sterilization, Program for Applied Research on Fertility Regulation Northwestern University Medical School, Chicago, Illinois, Contraception (United States), Mar. 1985, pp. 243–252 (Abstract).

Guenther et al., "The Apparent Molar Dilution of Precipitation Reactions Exemplified by the Reaction of Sodium Chloride and Silver Nitrate in Aqueous Solution", Zeitshcriff fuer Physikalische Chemie Neue Folge, pp. 24–37 (1973).

HCAPLUS Abstract 1977:522810 (Corey) 1977.*

CA Abstract 79: 149392 (Wiese, G. et al.) 1973.*

Scroggs, M.W. et al., Pediatric Pathology, vol. 10, pp. 319–333. 1990.*

* cited by examiner

INTRAUTERINE CHEMICAL CAUTERIZING METHOD AND COMPOSITION

This application is a continuation of U.S. patent application Ser. No. 08/486,561, filed Jun. 7, 1995 now abandoned.

BACKGROUND OF THE INVENTION

1. Field of the Invention

This invention relates to a method and composition for chemically cauterizing the tissue lining of a human body cavity, particularly the endometrial mucosa of the uterus. More specifically, the methods and compositions of the present invention provide effective cauterization of the endometrium of a mammalian uterus without many of the disadvantages and dangerous features of known intrauterine cauterization techniques.

2. The Prior Art

The following terms as used herein have the meaning given below:

"Necrosis" means the death of cells in a tissue.

"Endometrium" is that portion of the inner lining of the uterus to which an embryo normally attaches and excludes the portions of the uterine inner lining forming the cervix, to which the embryo usually does not attach.

"Cryogenic" is used to refer to temperatures sufficiently low to cause necrosis.

Apparatus and methods for cauterization of the endometrium of a mammalian uterus, useful in sterilization procedures and cancer treatments, are well known. Thermal and cryogenic treatments have been utilized in such cauterization techniques and typically involve either the direct or indirect application of heat or cold to the tissue to be treated.

For example, a laser hysteroscope has been used to cauterize the endometrial layer of the uterus. This laser treatment suffers from several disadvantages. It requires the application of an intense amount of thermal energy to a relatively small area of tissue even though such a large amount of heat may not be necessary to effectively cauterize the tissue. Further, this laser treatment requires the physician to continually re-position the laser under hysteroscopic control used in the treatment within the uterus in order to treat the entire endometrium. Such internal manipulation of a laser hysteroscope within the uterus of a patient is both difficult, requiring a significant level of skill to perform, and potentially dangerous. Accidental puncture of the uterine or tissue wall may result from manipulation of the laser scope within the uterus or body cavity, and tissue layers beneath the endometrium may be burned through the entire thickness if a laser's beam is left focused on one area of tissue for too long a period of time. Electrosurgical endometrial ablation functions on a similar principle and suffers similar risks as laser endometrial ablation.

A variety of alternatives to laser treatment in cauterizing the uterine endometrium are known. In U.S. Pat. Nos. 4,949,718 and 5,105,808 to Neuwirth et al. a method and device for effecting the necrosis of the tissue lining of a mammalian body cavity, particularly the uterine endometrium by heating the liquid contents of an inflated distendable bladder inside the uterine cavity is disclosed. Inflating the distendable bladder inside the uterus allows for contact between the distendable bladder wall and the endometrial lining. However, the distendable bladder is not effective in contacting all of the endometrial lining. Although the distendable bladder may conform to the general shape of the uterus, due to the irregular surface of the endometrial mucosa and the endometrial cavity, the inflated distendable bladder may not contact all of the uterine endometrium.

U.S. Pat. No. 3,924,628, to Droegemueller et al. discloses a method and apparatus for necrosing tissue cells that utilizes an extendable bladder which is inserted in the uterus and filled with a circulating fluid or gas at cryogenic temperatures (referring to temperatures sufficiently low to cause cell necrosis). The bladder disclosed by Droegemueller et al. is maintained in substantially continuous contact with the inner surface of the uterine lining and achieves necrosis of substantially all of the uterine endometrium in a single treatment. Droegemueller et al. disclose the use of liquid nitrogen that vaporizes prior to introduction into the bladder, thereby pressurizing the bladder to a level which ensures adequate contact with the uterus. Other fluids disclosed by Droegemueller et al. as useful in their method include refrigerants such as freon. Droegemueller et al.'s method and apparatus suffers from the disadvantage of employing cryogenic fluids which are toxic and could prove fatal to a patient in the event of bladder rupture. Moreover, Droegemueller et al.'s apparatus does not allow regulating the pressure used to inflate the bladder. In the event of a bladder rupture, the cryogenic fluid would rapidly change state from a liquid to a gas with possible grave consequences for the patient. Another disadvantage of Droegemueller et al.'s technique is that it does not limit the amount of cryogenic fluid that would be introduced into the uterus in the event of a bladder rupture.

In U.S. Pat. No. 2,734,508, Kozinski discloses a therapeutic apparatus for applying dry heat to body cavities comprising an applicator that is introduced in the body cavity while deflated and which is subsequently inflated and heated by means of circulating hot air. Kozinski does not disclose an applicator which conforms to the shape of a body cavity. Further, given the lower heat transfer coefficients of gases as compared with liquid, treatment with Kozinski's apparatus should involve a long period of time in order to achieve necrosis, thereby exposing the patient to additional discomfort and risk. Moreover, Kozinski's apparatus does not provide for measurement and regulation of internal pressures and temperatures of the applicator introduced.

U.S. Pat. No. 2,077,453, issued to Albright, discloses a therapeutic appliance comprising a relatively long tubular applicator which is shaped and formed generally to the passage into which it is to be inserted and which has relatively thin elastic rubber walls that transfer heat and which distend to fit irregularities of the treated areas upon application of internal pressure. Albright also discloses that fluids such as heated water could be utilized as a heating means in his applicator. The applicator of Albright, like that of Kozinski, however, suffers from the disadvantage that the distension of its walls to conform to the irregularities of the endometrium is limited as Albright provides an integral rubber web which serves to prevent undue distension of the applicator. Moreover, Albright requires that the fluid be circulated throughout the apparatus. Albright also does not provide an apparatus that allows regulation of temperature and pressure of the fluid or other bladder inflation means.

U.S. Pat. No. 3,369,549, issued to Armao, discloses a therapeutic device for applying heat or cold to body cavities comprising a capsule probe containing a heat exchanger and a flexible bladder that can be inflated to conform to a body cavity. Armao does not, however, disclose a control means for regulating the temperature and pressure of the flexible applicator, nor does he disclose cauterizing tissue in the cavity being treated.

Other patents that disclose the use of thermal treatment of the interior lining of a body cavity include U.S. Pat. Nos. 2,192,768; 2,466,042; 2,777,445; and 3,369,549.

In addition to these thermal and cryogenic treatments, application of caustic chemicals to achieve sterilization and treat cancers is also known. The use of caustic chemicals as locally destructive agents has been attempted but has been limited by concerns about safety and control of the delivery of various agents as well as other shortcomings due to the methods of application, e.g., blind placement of a particular solid chemical. For example, as described by Babcock, W., *Chemical Hysterectomy*, Jnl. Obstet. & Gyn., Vol. 7, 1924, application of gauze strips soaked in a saturated solution of zinc chloride to the uterine walls has been used to produce amenorrhea, to produce sterility, and to treat tumors. However this procedure has several disadvantages. Initially, it is noted that the application of the gauze strips is a blind procedure. The zinc chloride soaked gauze is packed in the uterus until the practitioner feels the cavity is full. The strips are left in place for a predetermined length of time and then removed. Delivery to and removal from the uterine cavity of the caustic gauze strips necessarily entails substantial risk of contacting the vaginal walls wherein the caustic agent could damage the vaginal and other tissue which is not the target of the treatment. Accordingly, successful use of this methodology requires substantial skill and experience, limiting the availability of the procedure to women with access to highly trained medical personnel.

Use of caustic agents such as silver nitrate, zinc chloride and copper sulfate has been studied for use in chemical sterilization by chemically cauterizing the fallopian tubes. However, as discussed by Richart, R., *Female Transcervical Sterilization*, Chapter 3, Harper & Row (1983), even when massive tubal necrosis was achieved with the application of silver nitrate ($AgNO_3$), a significant proportion of fallopian tubes remained open. When compositions for the sustained release of the caustic agents were employed it was found that control over the release of the caustic agents was insufficient to avoid unacceptable side effects. Additionally, use of strong caustic agents such as acids and alkalies would require the concomitant use of equally strong neutralizing agents whose use is also laden with risk. Use of such agents also puts the practitioner in the difficult position of titrating the neutralization of the caustic agent in the patient's uterus.

SUMMARY AND OBJECTS OF THE INVENTION

It is an object of the present invention to provide a safe and efficacious method for chemically cauterizing the tissue lining of a body cavity, particularly the endometrium of a uterus.

It is another object of the present invention to provide a relatively inexpensive and easy to use paste composition of a caustic agent and a non-toxic carrier, which is easily and safely neutralized, that can be used to effect chemical cauterization of lining of a mammalian body cavity.

It is yet another object of the present invention to provide a relatively inexpensive and easy to use paste composition of silver nitrate and a non-toxic carrier, which is easily and safely neutralized, that can be used to effect chemical cauterization of the uterine endometrium.

It is still another object of the present invention to provide a method for introducing a controlled amount of silver nitrate paste under predetermined pressure into a uterine cavity so as to increase the likelihood of the silver nitrate making substantially uniform and intimate contact of the paste with the endometrium for a predetermined time.

It is another object of the present invention to provide a method for effecting chemical cauterization necrosis of the tissue lining of a mammalian body cavity comprising the steps of inserting a hysteroscope into the body cavity; passing an inert gas or non electrolyte liquid medium through the hysteroscope to expand the body cavity; applying to the tissue to be treated a caustic paste sufficiently caustic to effect cauterization of the tissue to be treated, spreading the caustic paste substantially uniformly over the tissue surface under observation through the hysteroscope so that the paste is in contact with substantially all of the tissue lining for which necrosis is desired; allowing the fluid or gas used to expand the body cavity to exit the body cavity so as to return the body cavity to its relaxed state thereby further aiding in the distribution of the caustic paste over the tissue surface; allowing the caustic paste to remain in the body cavity for a period of time sufficient to effect chemical cauterization necrosis of substantially all of the tissue lining of the body cavity for which necrosis is desired; delivering to the tissue lining a neutralizing solution for neutralizing the caustic substance to substantially inert components and rinsing the neutralized caustic from the body cavity.

It is yet another object of the present invention to provide a method for effecting chemical cauterization necrosis of the tissue lining of a mammalian uterus comprising the steps of inserting a hysteroscope into the uterus; passing $CO_2$ gas to expand the uterus through the hysteroscope; passing through the hysteroscope a first catheter for delivery of a predetermined volume of silver nitrate paste and a second catheter for delivery of an aqueous sodium chloride solution for neutralizing the silver nitrate paste; spreading the silver nitrate paste substantially uniformly over the endometrium under observation through the hysteroscope so that lining of the paste is in contact with substantially all of the endometrium; allowing the $CO_2$ gas used to expand the uterus to exit the uterus returning the uterus to its relaxed state thereby further aiding in the distribution of the silver nitrate paste over the endometrial surface as the uterus contracts; allowing the silver nitrate paste to remain in the uterus for a period of time sufficient to effect chemical cauterization necrosis of substantially all of the endometrial lining of the uterus; delivering to the body cavity through the second catheter an aqueous sodium chloride solution for neutralizing the silver nitrate paste to substantially inert silver chloride and rinsing the silver chloride from the uterus by tidal flow or continuous sodium chloride rinsing or irrigation washing.

It is still another object of the present invention to provide a method for effecting chemical cauterization necrosis of the tissue lining of a mammalian body cavity comprising the steps of inserting a catheter into the body cavity; delivering a caustic paste into the body cavity to the natural fill volume of the body cavity through the catheter, not to exceed a predetermined volume or pressure; regulating the pressure of the caustic paste by control means connected to the catheter; and maintaining the paste so inserted for a period of time sufficient to effect chemical cauterization necrosis of substantially all of the tissue lining of the body cavity for which necrosis is desired; delivering to the body cavity through the catheter a neutralizing solution for neutralizing the caustic to substantially inert components and removing the neutralized caustic from the body cavity via tidal flow or continuous sodium chloride rinsing or irrigation washing.

The present invention also provides a method for effecting chemical cauterization necrosis of the endometrium of a mammalian uterus comprising the steps of inserting first and second catheters into the uterus; delivering between approximately 5 ml and 15 ml of a silver nitrate paste into the uterus not to exceed the natural fill volume of the uterus, through the first catheter, not to exceed a predetermined pressure which should be below tubal opening pressure; regulating the pressure of the silver nitrate paste by control means connected to the catheter; and maintaining the silver nitrate paste so inserted for a period of time sufficient to effect cauterization necrosis of substantially all of the uterine endometrium; delivering to the uterus through the second catheter an aqueous sodium chloride solution for neutralizing the silver nitrate to substantially inert silver chloride and rinsing the silver chloride from the uterus.

It is another object of this invention to provide a method for treating the endometrial mucosa of a uterus, comprising the steps of applying a caustic composition to the endometrial mucosa of a uterus; allowing the caustic composition to remain in contact with the endometrial mucosa for a period of time sufficient to effect cauterization necrosis of the endometrial mucosa; contacing the caustic composition with a neutralizing agent to neutralize the caustic composition; and withdrawing the neutralized caustic composition and the neutralizing agent from the uterus.

It is another object of this invention to provide a method for treating the endometrial mucosa of a uterus, comprising the steps of applying a silver nitrate composition to the endometrial mucosa of a uterus; allowing the silver nitrate composition to remain in contact with the endometrial mucosa for a period of time sufficient to effect cauterization necrosis of the endometrial mucosa; contacting the silver nitrate with a solution of sodium chloride to neutralize the silver nitrate; and withdrawing the neutralized silver nitrate and the sodium chloride from the uterus.

It is yet another object of this invention to provide a composition for treating the endometrial mucosa of a uterus, comprising about 10% to about 50% by weight silver nitrate; about 35% to about 80% by weight dextran and; about 0% to about 55% weight $H_2O$.

DETAILED DESCRIPTION OF THE INVENTION

Figure 1:
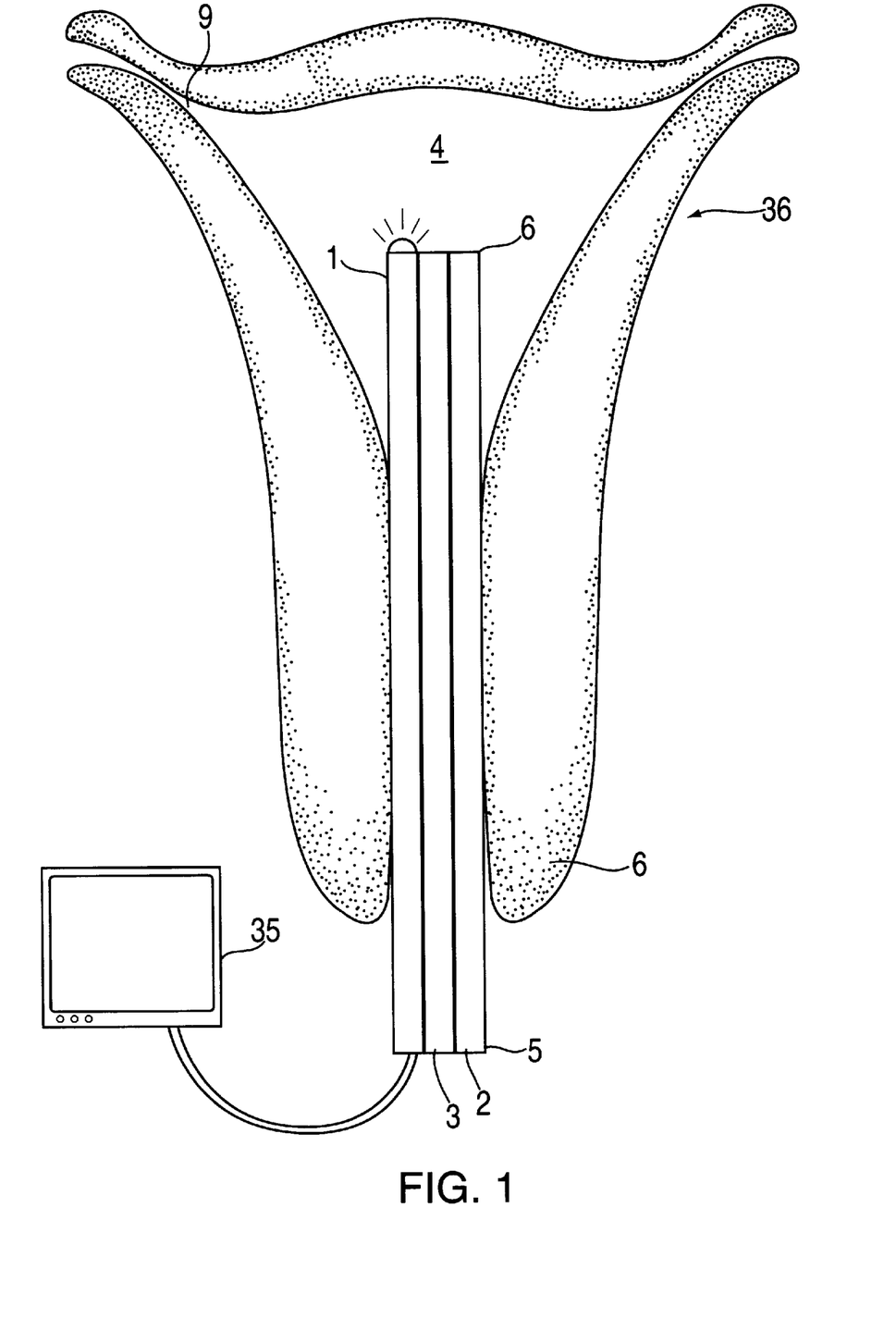
FIG. 1 shows one embodiment of the invention in which a hysteroscope has been inserted into a mammalian uterus.

FIG. 1 shows a hysteroscope 1 provided with a first catheter 2 and second catheter 3 passing therethrough. The hysteroscope 1 has a proximal end 5 and a distal end 6 with the distal end 6 being located within the uterine cavity 4 of a mammalian uterus 36. While the external diameter of the hysteroscope 1 must be sufficiently small so that it can be safely and conveniently inserted into the uterine cavity 4 through a partially dilated cervix 6, it must have an internal diameter sufficiently large to accommodate the first and second catheters 2 and 3. The external diameter of the hysteroscope 1 must be sufficiently wide so as to make a substantially air and liquid tight seal with the cervix 6. In order to allow for easy insertion, this seal may be created by employing any one of several devices well known to those skilled in the art such as a contracervical cap, an intracervical balloon, or an intracervical plug. The proximal end 5 of the hysteroscope 1 may be adapted in any one of several ways well-known to those skilled in the art to allow for the free manipulation of the first catheter 2 to provide more accurate delivery of the caustic paste (as shown in FIG. 3) and also allow for the selective delivery of gas or liquid through the second catheter 3 to both expand the uterine cavity 4 before treatment and to flush the uterine cavity with a neutralizing agent 4 after treatment, as shown in FIGS. 2 to 4.

Figure 2:
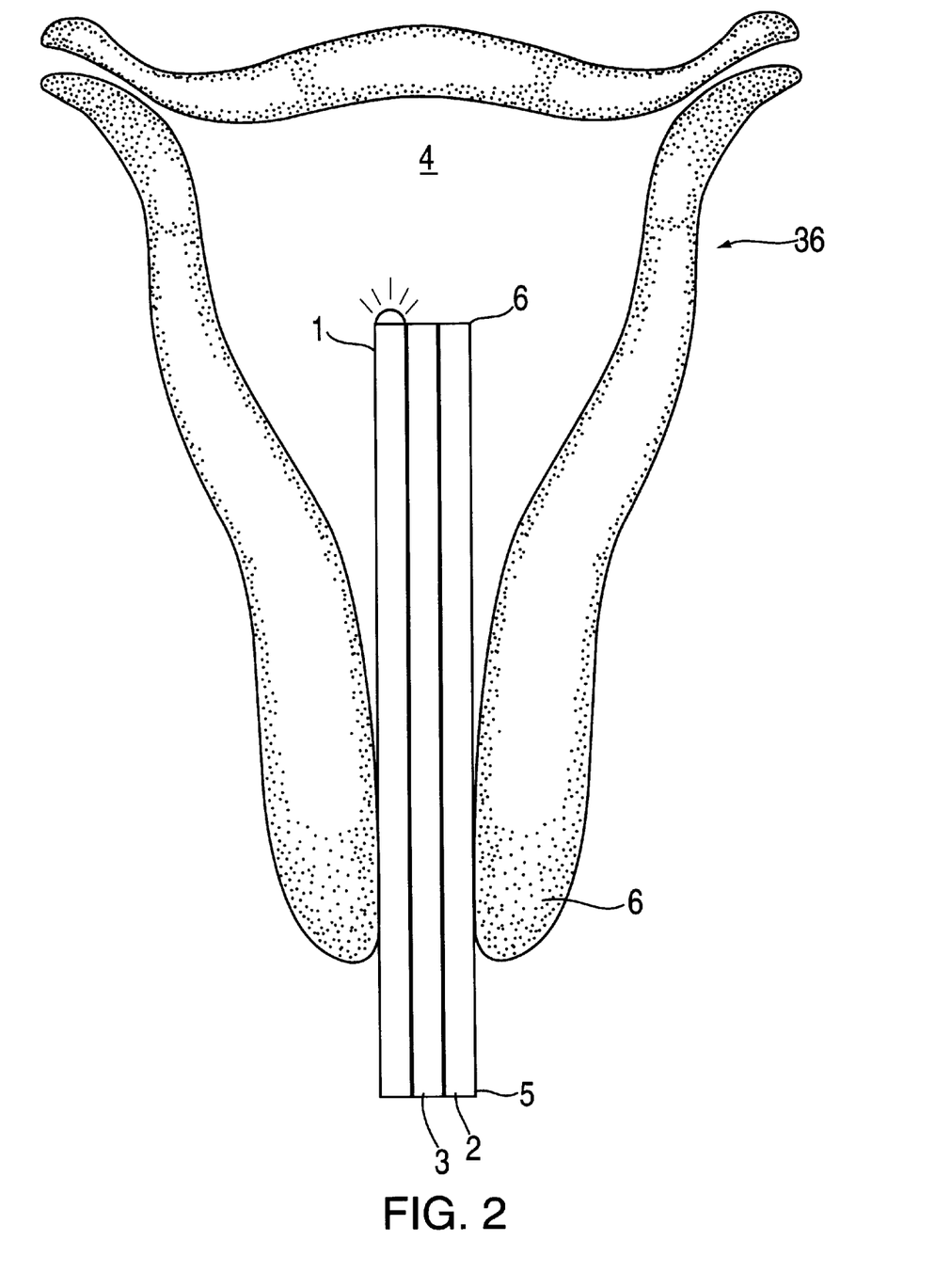
FIG. 2 shows the embodiment of the invention shown in FIG. 1 and shows the distended uterine cavity after it has been expanded prior to delivery of the caustic paste.

As shown in FIG. 1, the hysteroscope 1 housing the first catheter 2 and the second catheter 3 is aligned with the cervical canal after the cervix 6 is exposed with a speculum and grasped with a tenaculum. After the hysteroscope 1 has been inserted into the uterine cavity 4, an inert gas, preferably $CO_2$, or a non electrolyte liquid, is pumped into the uterine cavity 4 via second catheter 3 to a pressure sufficient to ensure expansion of the uterine cavity 4, as shown in FIG. 2. This allows the physician to visualize the application of the silver nitrate paste 7 to the endometrial tissue layer on the interior endometrial surface of the uterine cavity 4 on monitor 35. The pressure of the $CO_2$ should preferably be maintained at a pressure of about 30 to about 50 mmHg, and preferably about 40 mmHg, to maintain the uterus in the expanded state while minimizing the risk of damage to the uterine wall and minimizing the risk of overcoming fallopian tubal opening pressure. The pressure of the $CO_2$ is regulated by an expansion medium pressure control means (not shown).

Figure 3:
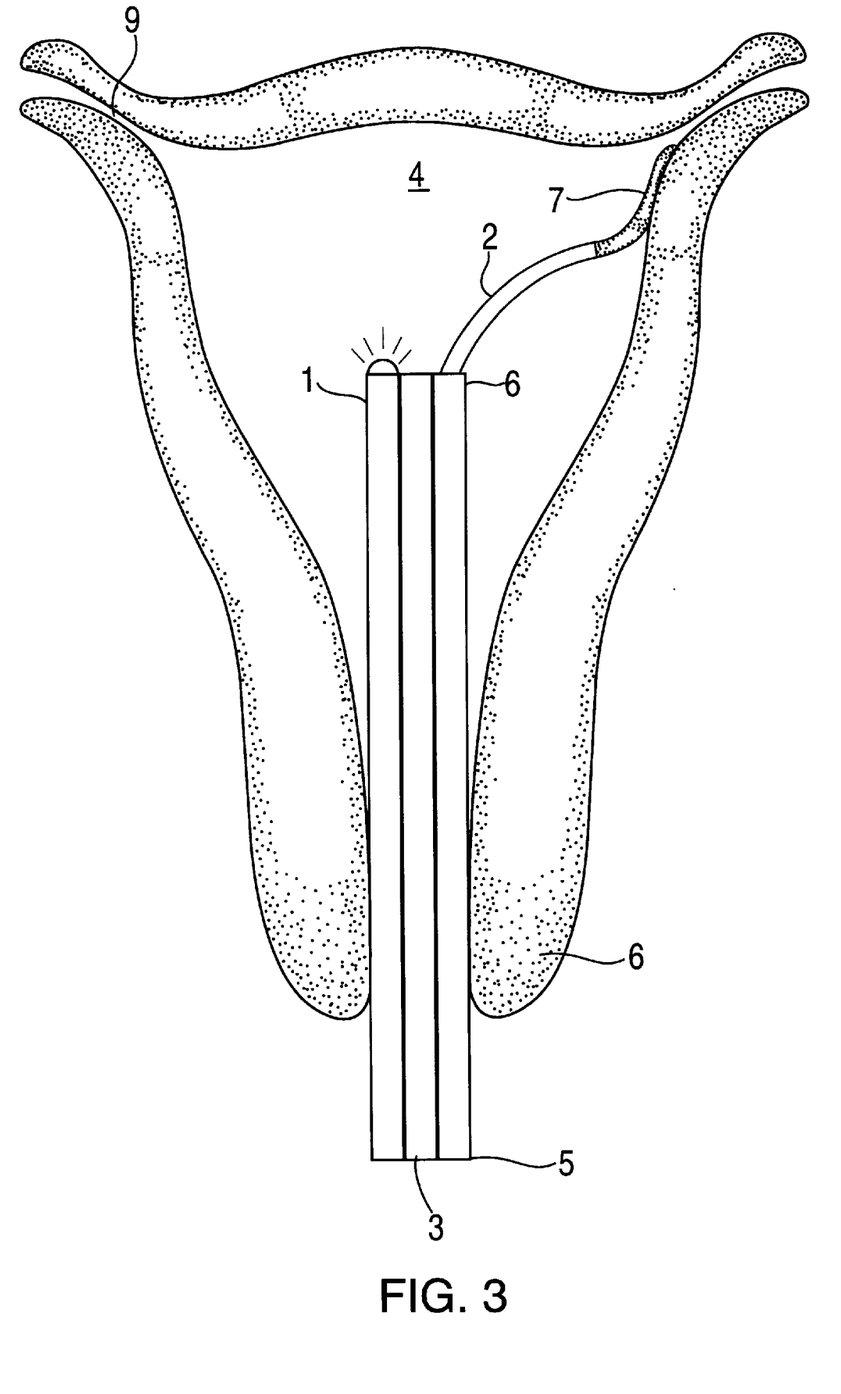
FIG. 3 shows the embodiment of the invention shown in FIGS. 1 and 2 and shows a caustic composition being applied to the endometrial mucosa.

After the uterine cavity 4 has been expanded, the caustic paste, e.g., silver nitrate 7, may be applied to the tissue to be treated as shown in FIG. 3. The first catheter 2 disposed within the hysteroscope 1 may be extended through an opening located at the distal end 6 of the hysteroscope 1. The delivery of the silver nitrate paste 7, may be accomplished through the first catheter 2, preferably a 2 mm catheter, under hysteroscopic control and preferably in a carbon dioxide gas environment. The paste is a mixture of caustic agent sufficient to effect necrosis of substantially all of the subject tissue, an inert carrier, and the balance a non reactive fluid. In a preferred embodiment, the composition comprises about 10 to 50% by weight caustic agent and about 35 to 80% by weight inert carrier to form a fluid paste. In an especially preferred embodiment the paste is 10 to 50% by weight caustic agent and about 35 to 80% by weight dextran 70 or dextran 40 and water. Most preferably, the paste is 10 to 50% by weight silver nitrate and 35 to 80% by weight dextran 70 or dextran 40 and water. The paste may be mixed to any level of viscosity suitable for the specific application and the introduction and withdrawal devices used in the process. By increasing the dextran 70 or dextran 40 to water ratio the paste will become more viscous and may be more difficult to pass through syringes or catheters with narrow bores.

Figure 4:
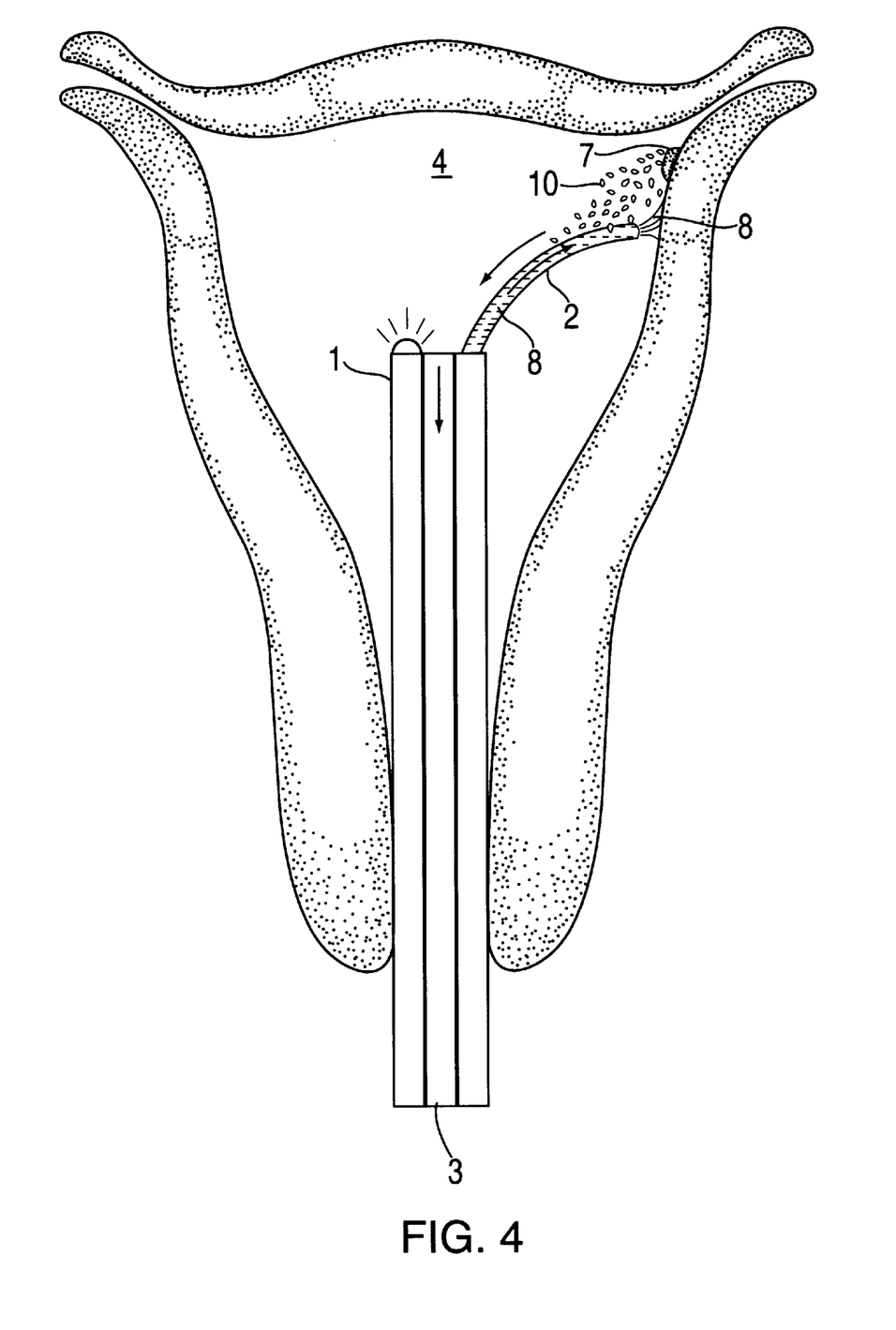
FIG. 4 shows the embodiment of the invention shown in FIGS. 1, 2 and 3 in which the neutralized caustic composition is flushed from the surface of the endometrium after treatment.

The hysteroscope 1 is connected to a monitor 35 which allows the practitioner to observe the procedure and assure that the silver nitrate paste 7 is applied to the target tissue to be treated. The effect of the silver nitrate paste 7 can be observed as is currently done using laser or electrosurgical coagulation of the endometrium using a hysteroscope. After application of the paste 7 is completed, the $CO_2$ distending the uterine cavity 4 is evacuated through second catheter 3 which returns the uterine cavity 4 to its relaxed state. This allows the opposing internal walls of the uterus 36 to contact each other thereby further distributing the silver nitrate paste 7. After sufficient time has elapsed to bring about endometrial necrosis to a depth of approximately 5 mm, a neutralizing agent, e.g., an aqueous solution of sodium chloride 8, preferably about 5% by weight sodium chloride, is introduced through the first catheter 2 under a positive pressure of about 30 to 40 mmHg, as shown in FIG. 4, to neutralize any remaining active silver nitrate paste 7. The silver nitrate 7 and sodium chloride 8 will react to form inert silver chloride 10. By washing the uterine cavity 4 with excess aqueous sodium chloride solution 8, about 2 to 3 liters, complete neutralization of the silver nitrate paste 7 is promoted. Two methods for washing the uterine cavity 4 are preferred. During tidal washing, the sodium chloride solution 8 is delivered and withdrawn through the same catheter, e.g., 3. The sodium chloride solution 8 should be delivered at pressures below fallopian tubal opening pressure to limit the possibility of washing any remaining silver nitrate 7 into the fallopian tubes 9. After waiting a sufficient period of time for the sodium chloride solution 8 to neutralize the silver nitrate paste 7 into silver chloride 10, the sodium chloride solution 8, silver chloride 10, and any remaining silver nitrate paste 7 may be withdrawn under negative pressure, approximately negative 1 to 2 mmHg, applied to the second catheter 3. The negative pressure should be low enough to minimize the risk of collapsing the uterine cavity 4.

Alternatively, irrigation washing of the uterus 4 is accomplished via a simultaneous inflow of fresh sodium chloride solution 8 and outflow of used sodium chloride solution 8, silver chloride 10, and any remaining silver nitrate 7. As shown in FIG. 4, irrigation washing may be accomplished, e.g., by delivering the fresh sodium chloride wash 8 through the first catheter 2 under positive pressure of approximately 30 to 40 mmHg and withdrawing the outwash through the second catheter 3 under negative pressure of about negative 1 to 2 mmHg. The sodium chloride solution 8 may also be introduced via second catheter 3 and withdrawn via first catheter 2 so as to prevent the introduction into the uterine cavity 4 of any silver nitrate remaining in first catheter 2. Alternatively, the practitioner may remove the contracervical cap, intracervical balloon, an intracervical plug utilized to seal the uterine cavity 4 and allow the washout to exit the uterine cavity 4 around the hysteroscope 1 rather than using negative pressure applied to the first catheter.

Most of the inert silver chloride 10 will be washed out of the uterine cavity 4 during the wash procedure and any remaining silver chloride 10 will be expelled from the body via natural processes.

This embodiment of the invention will now be illustrated by the following example.

EXAMPLE

The cauterization procedure is preceded by screening against cancer of the affected region and physical condition within established norms. A PAP smear and endometrial biopsy/curettage must exclude cancer or precancerous lesions of the uterus and cervix. If a fibroid uterus is present, an ultrasound should exclude ovarian masses.

The patient should be post menstrual or start on gonadotropin agonist or Danazol, or the equivalent which causes reduction in bleeding and a thin endometrium, at a rate of 800 ml daily, from the 5th day of the previous menstrual period until two weeks after the procedure. The patient will undergo the procedure in the ambulatory surgery unit or out-patient facility where Valium and/or Demerol can be given intravenously if there is pain during the chemical cauterization phase of the procedure.

The hysteroscope will be inserted after a bimanual examination and speculum of the cervix. Dilation to 6 mm may be required which may necessitate a local 1% by weight lidocaine block of the cervix. Placement of the hysteroscope may be facilitated by distance markings on the housing indicating depth of insertion.

The placement of the hysteroscope should create a substantially gas tight seal between the inner wall of the cervix and the outer wall of the hysteroscope and is achieved by using an intracervical balloon.

The practitioner then proceeds to expand the uterine cavity by delivering $CO_2$ through the second catheter disposed within the hysteroscope into the uterine cavity. The practitioner injects the $CO_2$ into the uterus until the pressure indicating means indicates that the internal pressure of the uterus is within the pre-set constraints. At that point, the practitioner manipulates a valve sealing the gas delivery pathway causing the uterus to remain expanded. The practitioner may then manipulate the first catheter under observation through the hysteroscope, to deliver the silver nitrate paste to the uterine endometrium. By viewing the process through the hysteroscope the practitioner increases the likelihood of delivering paste to substantially all of the endometrium.

The practitioner then manipulates the valve sealing the gas pathway to allow the $CO_2$ to escape from the uterine cavity returning the uterus to its relaxed state thereby promoting a complete distribution of the paste throughout the endometrium. The paste is allowed to stay in contact with the endometrium for a predetermined period of time or until the practitioner concludes that sufficient cauterization has taken place by observation through the hysteroscope. The period of time will vary depending on the concentration of the silver nitrate and the depth to which treatment is desired, however, for most applications a period of about 3 to about 15 minutes is preferred. In an especially preferred embodiment, a period of about 4 to about 6 minutes is utilized.

Upon completion of the procedure, an aqueous solution of sodium chloride is introduced into the uterus, e.g., through the second catheter to neutralize any remaining silver nitrate under positive pressure of 30 mmHG. The washout is then evacuated from the uterine cavity, e.g., through the first catheter under negative pressure of negative 1 mmHg.

It is noted that delivery of a caustic paste utilizing a hysteroscope allows for focal cauterization treatment as well as the described widespread cauterization of endometrial tissue.

It is also noted that the course of the cauterization may be monitored through the hysteroscope and may be arrested at any time by introduction of the aqueous sodium chloride solution.

Figure 5:
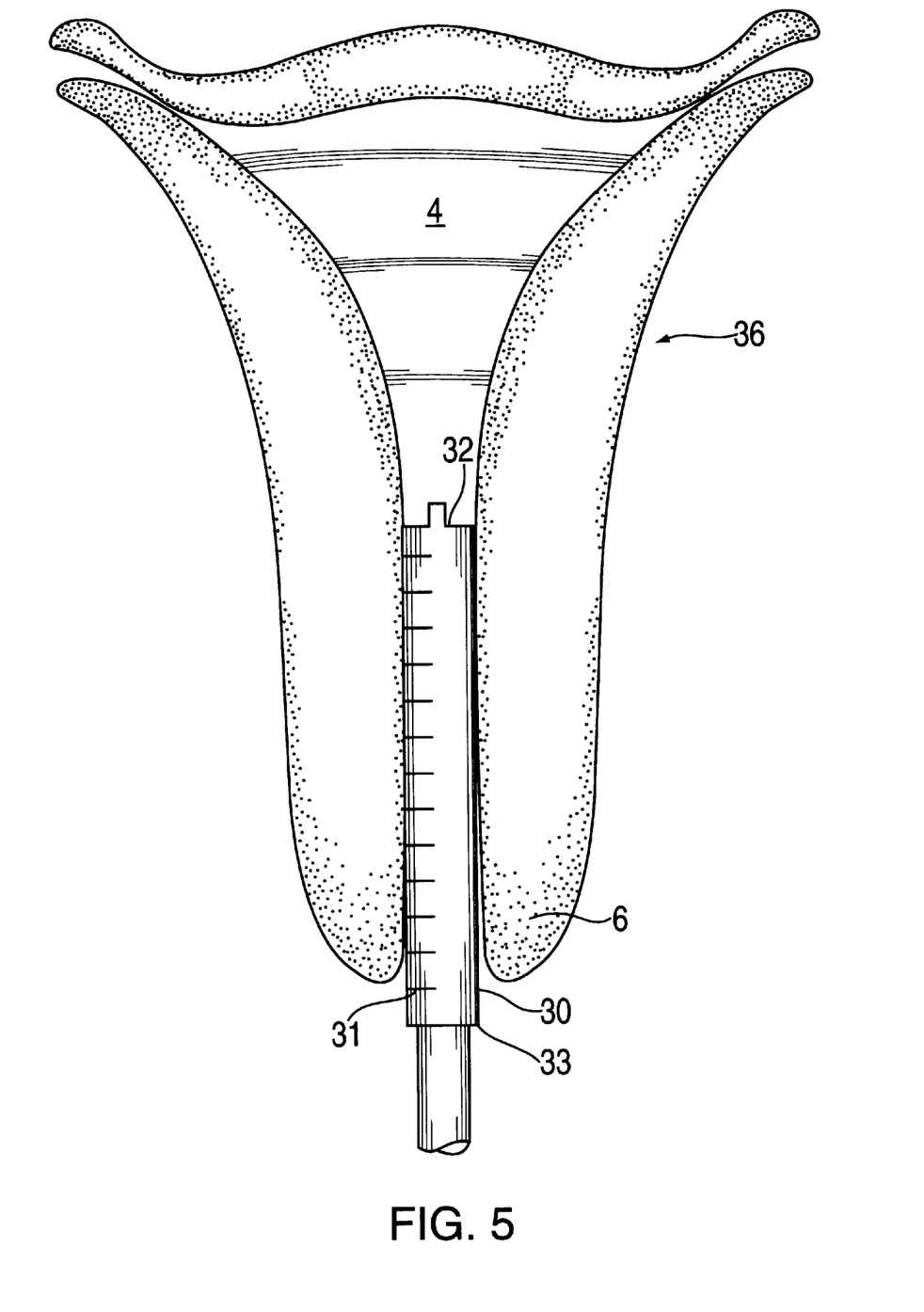
FIG. 5 shows another embodiment of the invention in which a catheter has been inserted into a mammalian uterus.

Another embodiment of the invention comprises the blind delivery of a silver nitrate paste 7 into the uterine cavity 4. As shown in FIG. 5, a catheter 30 is inserted past the cervical os, through the uterine canal for placement in the uterine cavity 4. Placement may be aided by virtue of scale gradations 31 located on the catheter 30 to indicate the depth of insertion of the catheter 30. The catheter 30 is preferably a 4 mm to 5 mm cannula approximately 20 cm long. The distal end 32 of the cannula may be provided with multiple perforations and the proximal end 33 is adapted to receive a syringe or other suitable device for delivering the silver nitrate paste 7.

Figure 6:
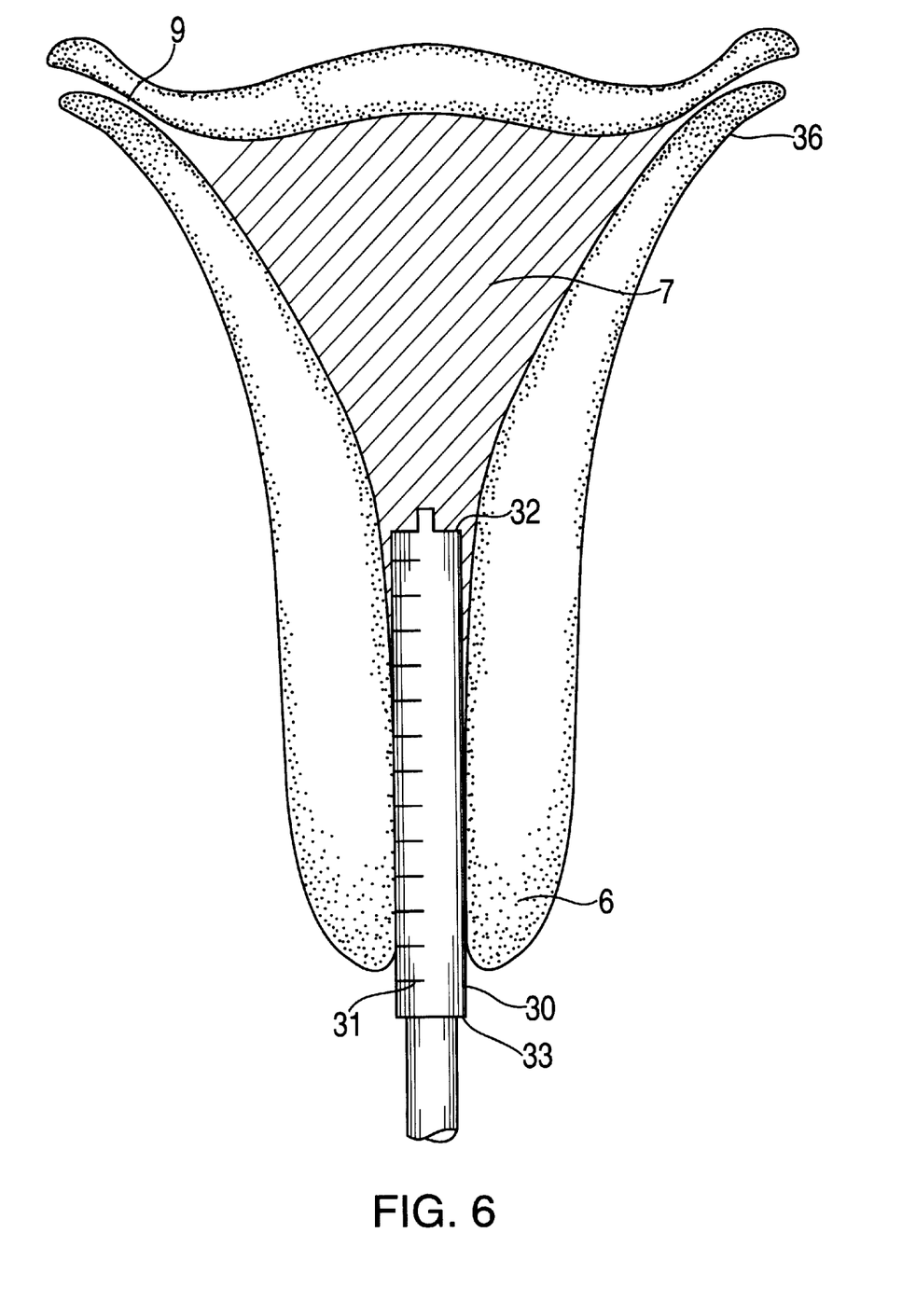
FIG. 6 shows the embodiment of the invention shown in FIG. 5 after the uterine cavity has been expanded by the delivery of the caustic paste.

As shown in FIG. 6, the silver nitrate paste 7 is injected into the uterine cavity 4 to substantially fill the entire volume of the cavity 4, thereby promoting intimate and substantially complete contact between the paste 7 and the endometrium lining the uterine cavity 4. The volume of paste injected should not exceed the natural fill volume of the uterine cavity 4, approximately 5 ml to approximately 15 ml, and the pressure applied in delivering the paste 7 should not result in an internal uterine pressure that exceeds fallopian tubal opening pressure of approximately 40 to 50 mmHg. The means for injecting the silver nitrate paste 7 is preferably fitted with a means to gauge the pressure being applied to the paste, i.e. a manometer, a spring, a pop off valve or a blister in the wall of the tube or syringe designed to control the pressure to the desired limit. When employing a silver nitrate paste 7, the procedure can be monitored by x-ray or sonography for control of localization and degree of filling.

The reaction maybe stopped and the uterine cavity may be washed by delivery of a sodium chloride solution as previously discussed. The speed and severity of the cauterization may be regulated by the percentage of the silver nitrate in the paste. By increasing the percentage of the silver nitrate in the paste the possibility for a deeper burn is increased. It is possible, by procedures well known to those skilled in the art, to determine the appropriate concentration of silver nitrate to achieve the desired depth of cauterization for specific applications. One of the benefits of this invention is that by employing silver nitrate, the practitioner may easily terminate the treatment by introducing a normal saline solution, NaCl, which will inactivate the silver nitrate by forming silver chloride. Alternatively, the practitioner could formulate a paste that is essentially self regulating. For example, a weak silver nitrate paste may be formulated that will expend itself after cauterizing to a depth of only half the maximum safely allowable depth, thereby reducing the danger of necrosing too deeply.

It is envisioned that a variety of caustic agents and their respective neutralizing agents may be used in this process. Caustic agents such as zinc chloride, phenol, iodine and various acids and alkalies are well known in the art and are applicable to the methods of this invention and may be inactivated by chemical reaction, removal, dilution or dosimetry.

It is also envisioned that in place of the second catheter of the first and second embodiments, the neutralizing solution may be delivered through the first catheter. In this variation the volume of neutralizing solution employed must be adjusted to account for the residual caustic paste that remains in the first catheter that will itself need to be neutralized.

What is claimed is:

1. A method for treating the endometrium of a uterus, comprising the steps of:
   a) applying a silver nitrate composition to the endometrium of a uterus;
   b) allowing the silver nitrate composition to remain in contact with the endometrium for a period of time sufficient to effect cauterization necrosis of the endometrium;
   c) contacting the silver nitrate composition with a solution of sodium chloride to neutralize the silver nitrate composition; and
   d) withdrawing the neutralized silver nitrate composition and the sodium chloride from the uterus.

2. The method of claim 1, wherein the silver nitrate composition is allowed to remain in contact with the endometrium for about 3 to about 15 minutes.

3. The method of claim 2, wherein the silver nitrate composition is allowed to remain in contact with the endometrium for about 4 to about 6 minutes.

4. The method of claim 1, further comprising the step of regulating the pressure at which the composition is applied so as to increase the likelihood that the composition will make contact with the endometrium and so as to reduce the likelihood that the composition will enter the fallopian tubes.

5. The method of claim 4, wherein the pressure is regulated to a pressure of about 40 to about 50 mm Hg.

6. The method of claim 1, wherein said silver nitrate composition has a viscosity at body temperature sufficiently fluid to cover the endometrium and sufficiently viscous at body temperature to reduce the likelihood that the silver nitrate composition will enter the fallopian tubes.

7. The method of claim 6, wherein said silver nitrate composition comprises a paste.

8. The method of claim 1 wherein said silver nitrate composition comprises silver nitrate and an inert carrier.

9. The method of claim 8, wherein said inert carrier comprises dextran.

10. The method of claim 1 wherein said silver nitrate composition comprises about 10% to about 50% by weight silver nitrate and about 35% to about 80% by weight inert carrier.

11. The method of claim 10, wherein said inert carrier comprises dextran.

12. The method of claim 1 wherein said silver nitrate composition comprises about 10% to about 50% by weight silver nitrate, about 35% to about 80% by weight dextran and about 0% to about 55% by weight $H_2O$.

13. A method for effecting chemical cauterization necrosis of the endometrium of a uterus, comprising the steps of:
   a) inserting a hysteroscope into the uterus, said hysteroscope adapted to permit observation of the procedure;
   b) passing $CO_2$ gas through the hysteroscope to expand the uterus;
   c) passing through the hysteroscope a first catheter adapted for delivery of a predetermined volume of a silver nitrate composition and a second catheter adapted for delivery of an aqueous sodium chloride solution for neutralizing the silver nitrate composition;
   d) spreading the silver nitrate composition over the endometrium under observation through the hysteroscope so that the silver nitrate composition is in contact with the endometrium;
   e) allowing the $CO_2$ gas used to expand the uterus to exit the uterus returning the uterus to its relaxed state thereby further aiding in the distribution of the silver nitrate composition over the surface of the endometrium as the uterus contracts;
   f) allowing the silver nitrate composition to remain in the uterus for a period of time sufficient to effect chemical cauterization necrosis of the endometrium of the uterus;
   g) delivering to the uterus through the second catheter an aqueous sodium chloride solution for neutralizing the silver nitrate composition to inert silver chloride; and
   h) removing the silver chloride from the uterus.

14. A method for effecting chemical cauterization necrosis of the endometrium of a uterus, comprising the steps of:

a) inserting first and second catheters into the uterus;
b) delivering through the first catheter between approximately 5 ml and 15 ml of a silver nitrate composition into the uterus;
c) regulating the pressure of the silver nitrate composition by control means connected to the first catheter to a pressure not to exceed a predetermined pressure below tubal opening pressure;
d) maintaining the silver nitrate composition so delivered into the uterus for a period of time sufficient to effect cauterization necrosis of the endometrium;
e) delivering to the uterus through the second catheter an aqueous sodium chloride solution for neutralizing the silver nitrate to inert silver chloride; and
f) removing the silver chloride from the uterus.

15. The method of claims 13 or 14 wherein the removing step is carried out by using a method selected from the group consisting of tidal flow, continuous sodium chloride rinsing, and irrigation washing.

* * * * *